United States Patent
Gunawan

(10) Patent No.: US 9,000,774 B2
(45) Date of Patent: Apr. 7, 2015

(54) NON-CONTACT CONDUCTIVITY MEASUREMENT

(71) Applicant: International Business Machines Corporation, Armonk, NY (US)

(72) Inventor: Oki Gunawan, Fair Lawn, NJ (US)

(73) Assignee: International Business Machines Corporation, Armonk, NY (US)

( * ) Notice: Subject to any disclaimer, the term of this patent is extended or adjusted under 35 U.S.C. 154(b) by 124 days.

(21) Appl. No.: 13/826,156

(22) Filed: Mar. 14, 2013

(65) Prior Publication Data

US 2014/0266248 A1 Sep. 18, 2014

(51) Int. Cl.
*G01R 27/32* (2006.01)
*G01N 27/04* (2006.01)
*G01N 27/72* (2006.01)

(52) U.S. Cl.
CPC ............... *G01R 27/32* (2013.01); *G01N 27/04* (2013.01); *G01N 27/72* (2013.01)

(58) Field of Classification Search
CPC ....... H02N 15/00; H02N 15/04; G01N 27/82; G01N 27/825; G01N 27/90; G01N 27/9046; G01N 9/36; H02K 49/10; G01B 7/087; G01B 7/10; G01R 15/148; G01D 5/147; G01D 5/202
USPC ........... 324/49, 691, 693, 719, 722, 439, 629, 324/649; 73/335.05
See application file for complete search history.

(56) References Cited

U.S. PATENT DOCUMENTS

| | | | |
|---|---|---|---|
| 3,992,938 A * | 11/1976 | Miller | 73/163 |
| 4,605,893 A | 8/1986 | Braslau | |
| 4,948,997 A * | 8/1990 | Ohmitsu et al. | 310/113 |
| 5,396,136 A * | 3/1995 | Pelrine | 310/90.5 |
| 5,404,062 A | 4/1995 | Hones et al. | |
| 5,485,405 A | 1/1996 | Wilson | |
| 5,692,329 A * | 12/1997 | Tang | 40/426 |
| 6,462,538 B2 | 10/2002 | Harada | |
| 6,819,120 B2 | 11/2004 | Tam | |
| 6,850,077 B2 | 2/2005 | Slates | |
| 7,197,946 B2 * | 4/2007 | Flammer et al. | 73/862.331 |
| 2006/0090564 A1 * | 5/2006 | Greene et al. | 73/504.02 |
| 2011/0294402 A1 | 12/2011 | Miller et al. | |
| 2013/0342191 A1 | 12/2013 | Gunawan | |

OTHER PUBLICATIONS

Y. Kraftmakher, "Eddy currents: Contactless measurement of electrical resistivity." American Journal of Physics, vol. 68, 2000, pp. 375-379.
A. Cansiz et al., "Stable Load-Carrying and Rotational Loss Characteristics of Diamagnetic Bearings," IEEE Transactions on Magnetics, vol. 40, Issue 3, May 2004, pp. 1636-1641.
H. Saotome et al., "Contactless Measurement of Sheet Resistance Using Impulse Voltage," IEEE Transactions on Magnetics, vol. 47, Issue 10, Oct. 2011, pp. 2581-2583.
Geim et al., "Magnet levitation at your fingertips", Nature, vol. 400, Jul. 22, 1999, pp. 323-324.
Smythe, Static and dynamic electricity, McGraw Hill, 1968, pp. 382-385.

* cited by examiner

*Primary Examiner* — Arleen M Vazquez
*Assistant Examiner* — Lee Rodak
(74) *Attorney, Agent, or Firm* — Cantor Colburn LLP; Vazken Alexanian

(57) ABSTRACT

A system for measuring the conductivity of a material-under-test includes a support structure, an upper magnet mounted to the support structure and a free-floating magnet below the fixed magnet. The system includes a diamagnet positioned between the fixed magnet and the free-floating magnet such that the free-floating magnet floats in the air beneath the diamagnet and a rotation detection assembly configured to detect a rotation rate of the free-floating magnet, where the rotation rate is based on a drag torque effect of a material-under-test on the free-floating magnet. The system also includes a conductivity calculation unit configured to calculate at least one of a conductivity or a resistivity of the material-under-test based on the detected rotation rate of the free-floating magnet.

13 Claims, 5 Drawing Sheets

NON-CONTACT CONDUCTIVITY MEASUREMENT

BACKGROUND

Embodiments of the invention relate generally to measuring conductivity and in particular to a non-contact conductivity measurement with a levitated magnetic rotor system.

Conductivity (or, inversely, resistivity) measurements of materials is routinely needed in many industries such as in semiconductor device fabrication, semiconductor circuit fabrication and various material inspection in manufacturing. Conventional conductivity and resistivity techniques require making contact with a material under test. In some applications, such as in-line process monitoring, it is necessary to have non-contact metrology techniques to measure the conductivity of a material under test due to speed requirements, the presence of insulating layers on the material-under-test or various other reasons.

SUMMARY

According to one embodiment of the invention, a system for analyzing a material-under-test includes a support structure, a mounted magnet mounted to the support structure and a free-floating magnet below the fixed magnet. The system includes a diamagnet positioned between the fixed magnet and the free-floating magnet such that the free-floating magnet floats in the air beneath the diamagnet and a rotation detection assembly configured to detect a rotation rate of the free-floating magnet, where the rotation rate is based on a drag torque effect of a material-under-test on the free-floating magnet. The system also includes a conductivity calculation unit configured to calculate at least one of a conductivity and a resistivity of the material-under-test based on the detected rotation rate of the free-floating magnet.

According to another embodiment of the invention, a method for analyzing a material-under-test includes levitating a free-floating magnet between a material-under-test and a diamagnet and a mounted magnet, such that the diamagnet is positioned between the mounted magnet and the free-floating magnet. The method also includes measuring a rotation rate of the free-floating magnet over time and calculating one of a conductivity and resistivity of the material-under-test based on the measured rotation rate of the free-floating magnet over time.

According to another embodiment of the invention a computer program product includes a computer readable medium having stored thereon computer code which, when executed by a processor, causes the processor to perform a method. The method includes initiating rotation of a free-floating magnet, where the free-floating magnet is suspended between a diamagnet and a material-under-test. The diamagnet is located between the free-floating magnet and a mounted magnet to cause the free-floating magnet to float. The method further includes measuring a rotation rate of the free-floating magnet over time and calculating at least one of a conductivity and a resistivity of the material-under-test based on the rotation rate of the free-floating magnet.

Additional features and advantages are realized through the techniques of the present invention. Other embodiments and aspects of the invention are described in detail. For a better understanding of embodiments of the invention, refer to the description and to the drawings.

BRIEF DESCRIPTION OF THE SEVERAL VIEWS OF THE DRAWINGS

Features characterizing embodiments of the present invention are described in the specification and claims which follow. These features, and advantages of embodiments of the invention are apparent from the following detailed description taken in conjunction with the accompanying drawings in which:

DETAILED DESCRIPTION

Conventional systems and methods require that contact be made with a material under test to measure the conductivity of the material. Embodiments of the invention are directed to measuring the conductivity of a material without physically contacting the material.

Figure 1:
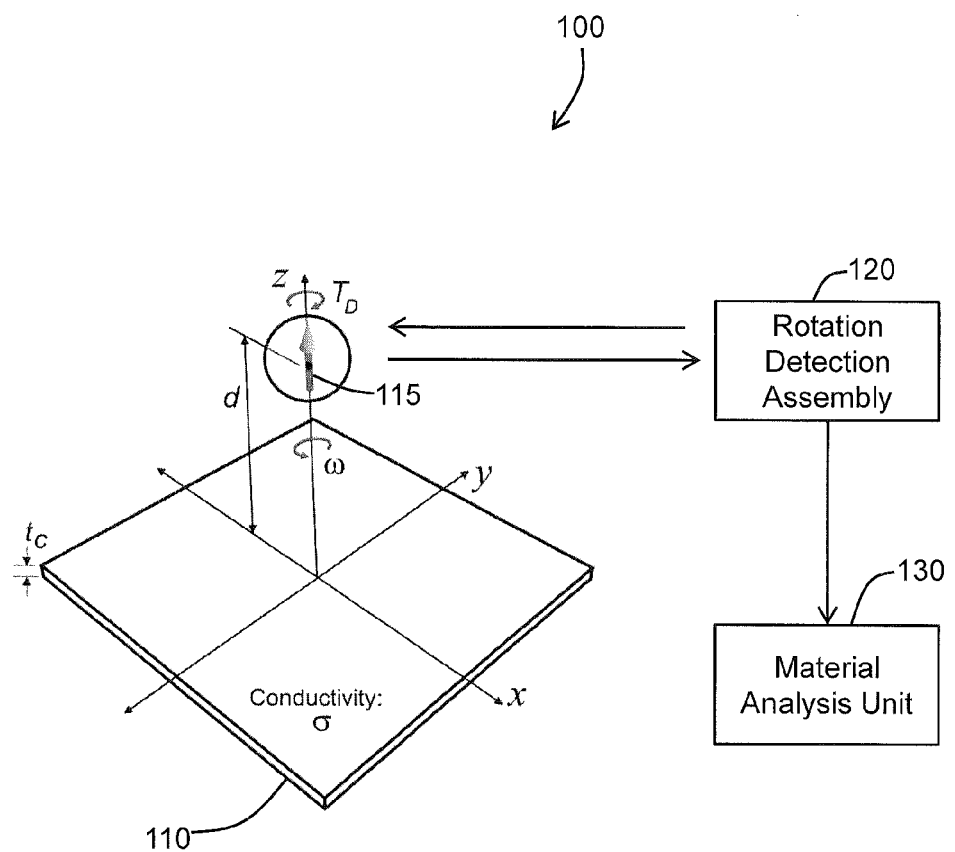
FIG. 1 illustrates a system for analyzing a material-under-test according to an embodiment of the invention.

FIG. 1 illustrates a system 100 for analyzing a material-under-test according to one embodiment of the invention. The system 100 includes a conductor or the material under test 110, a magnet 115 that levitates above the conductor 110 in a manner that will be described in further detail with respect to FIGS. 2A-4, a rotation detection assembly 120 and a material analysis unit 130.

If a magnetic dipole 115 rotates near a conductor 110, it will experience a braking or drag torque $T_D$ which is proportional to, but opposite to, the angular rotation speed $\omega$ of the magnet 115. Equation 1 defines drag torque $T_D$.

$$T_D = -\beta \sigma t_C \frac{\omega}{d^2} \quad (1)$$

In Equation 1, $\beta$ is a constant prefactor given as: $\beta = \mu_0^2 m^2 / 64\pi$. In addition, $\mu_0$ is the magnetic permeability in vacuum; m is the magnetic moment of the magnet; $\sigma$ is the conductivity of the conductor 110; $t_C$ is the thickness of the conductor 110; and d is the distance between the magnet 115 and the conductor 110.

Usually, the conductivity and thickness of a material may be combined into a single quantity called sheet conductivity: $\sigma_s = \sigma t_C$. In embodiments of the invention, as the magnet 115 rotates, the rotation rate is measured by a rotation detection assembly 120, and the drag torque $T_D$ is determined by the material analysis unit 130. The material analysis unit 130 may then calculate the conductivity or resistivity of the conductor 110.

Figure 2A:
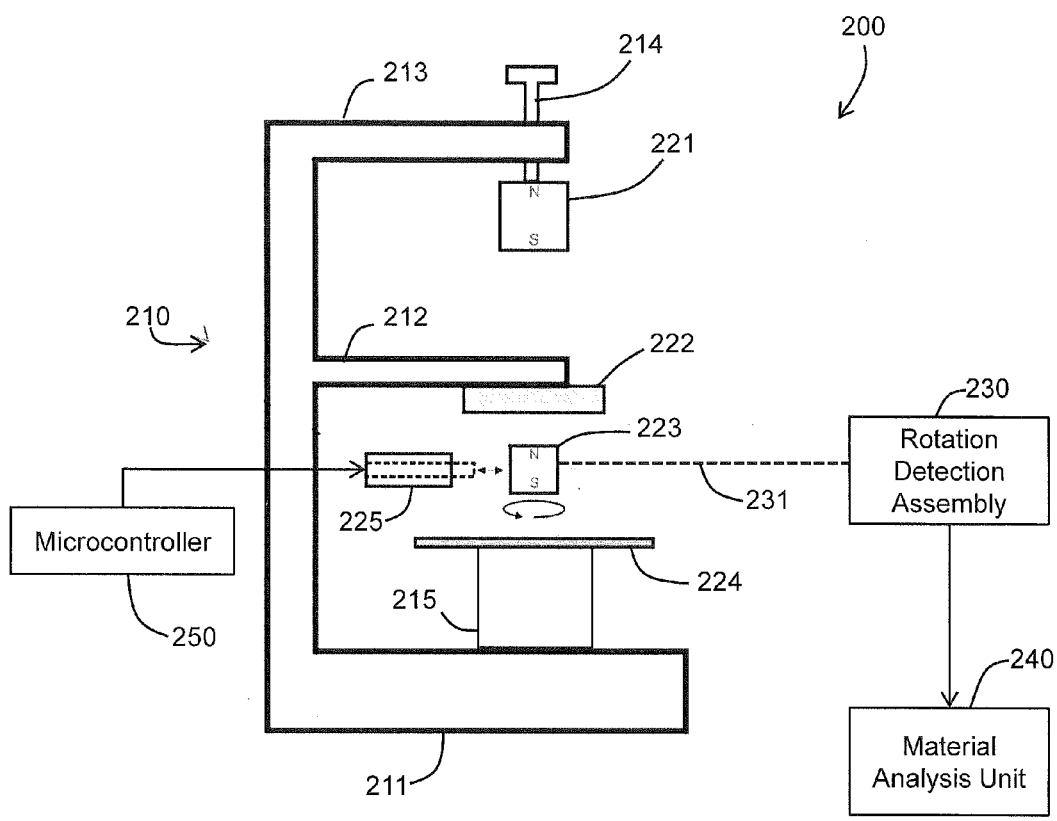
FIG. 2A illustrates a system for analyzing a material-under-test according to another embodiment of the invention.
Figure 2B:
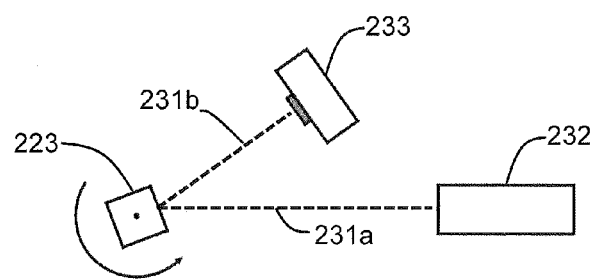
FIG. 2B illustrates the system for analyzing a material-under-test according to an embodiment of the invention.

FIGS. 2A and 2B illustrate a system 200 for analyzing a material-under-test 224 according to an embodiment of the invention. The system 200 includes a support structure 210 including a base 211, a first support arm 212 and a second support arm 213.

A material-under-test 224 is mounted to, or rests upon, a mounting portion 215 of the base 211. The material-under-test 224 may be a conductive material, a semiconductor device including a conductive material therein, photovoltaic materials or any other material. In one embodiment, the material-under-test 224 is a semiconductor-based circuit having a buried conductive layer. In such an embodiment, the conductivity or resistivity of the conductive layer may not be able to be measured by contact-based methods, such as by connecting electrical leads to the circuit.

A diamagnet 222 is mounted to the first support arm 212 and a mounted magnet 221 is mounted to the second support arm 213. In the embodiment illustrated in FIG. 2A, the mounted magnet 221 is mounted to the second support arm 213 via an adjustment screw 214. A floating magnet 223 is positioned between the diamagnet 222 and the material-under-test 224. The mounted magnet 221 is configured to attract the floating magnet 223, while the diamagnet 222 is configured to repel the floating magnet 223. The position of the mounted magnet 221 may be adjusted such that the floating magnet 223 maintains its position between the diamagnet 222 and the material-under-test 224. In other words, the attraction force exerted upon the floating magnet 223 by the mounted magnet 221 is exactly offset by the combination of the repelling force of the diamagnet 222 and gravity.

In the present specification and claims, the floating magnet 223 may also be referred to as a free-floating magnet. By "floating magnet 223" or "free-floating magnet 223", it is understood that no physical structure supports or contacts the floating magnet 223 during the conductivity-detection process.

While one support structure 210 is illustrated in FIG. 2A, embodiments of the invention encompass any number of support structures and any device capable of mounting a material-under-test 224 beneath a floating magnet 223, a diamagnet 222 and a mounted magnet 221, such that the floating magnet 223 floats between the diamagnet 222 and the material-under-test 224, and the diamagnet 222 is located between the mounted magnet 221 and the floating magnet 223. In addition, while an adjustment screw 214 is illustrated to adjust a position of the mounted magnet 221, the position of the mounted magnet 221 may be adjusted by any method, such as adjustment of a position of the second support arm 213 or any other method. In addition, in some embodiments, the position of the first support arm 212 may be adjusted.

In operation, an impulse actuator 225, such as a solenoid including a coil wound around an armature, is controlled, such as by a microcontroller 250 including a processor, to apply a force to an edge of the floating magnet 223 to cause the floating magnet 223 to rotate. The material-under-test 224 exerts torque drag on the floating magnet 223 according to a conductivity of the material-under-test 224, or according to the conductivity of a conductive layer on or in the material-under-test 224. The drag torque slows down the rotation of the floating magnet 223 exponentially according to the following equation:

$$\omega = \omega_0 e^{-t/\tau} \quad (2)$$

In Equation 2, $\tau$ is the time constant given as: $\tau = I/\beta \sigma t_C$ where $\omega_0$ is the initial angular velocity at t=0 and I is the moment inertia of the floating magnet 223. The rotation detection assembly 230 detects the rotation rate or angular velocity of the floating magnet 223 over time using a laser beam 231.

As illustrated in FIG. 2B, the rotation detection assembly 230 may be a tachometer including a laser device 232 to generate a laser beam 231a and to direct the laser beam 231a at the floating magnet 223. The rotation detection assembly 230 further includes a photosensor 233 that detects the reflected laser beam 231b. The frequency with which the reflected laser beam 231b is detected corresponds to the rotation rate or angular speed of the floating magnet 223. The rotation rate is provided to the material analysis unit 240, which calculates the conductivity or resistivity of the material-under-test 224, or a conductive layer on or in the material-under-test 224, based on the measured rotation rate. The material analysis unit 240 includes a processor, memory and supporting circuitry capable of receiving sensor signals from the rotation detection assembly 230, calculating a rotation rate based on the signals and calculating a conductivity or resistivity by applying the calculated rotation rate to a predefined algorithm, such as the algorithm of equation 1, above.

While the material analysis unit 240 and microcontroller 250 are illustrated as separate blocks for purposed of description, the microcontroller 250 and material analysis unit 240 may be part of the same computer, computing circuit or integrated circuit.

Figure 3:
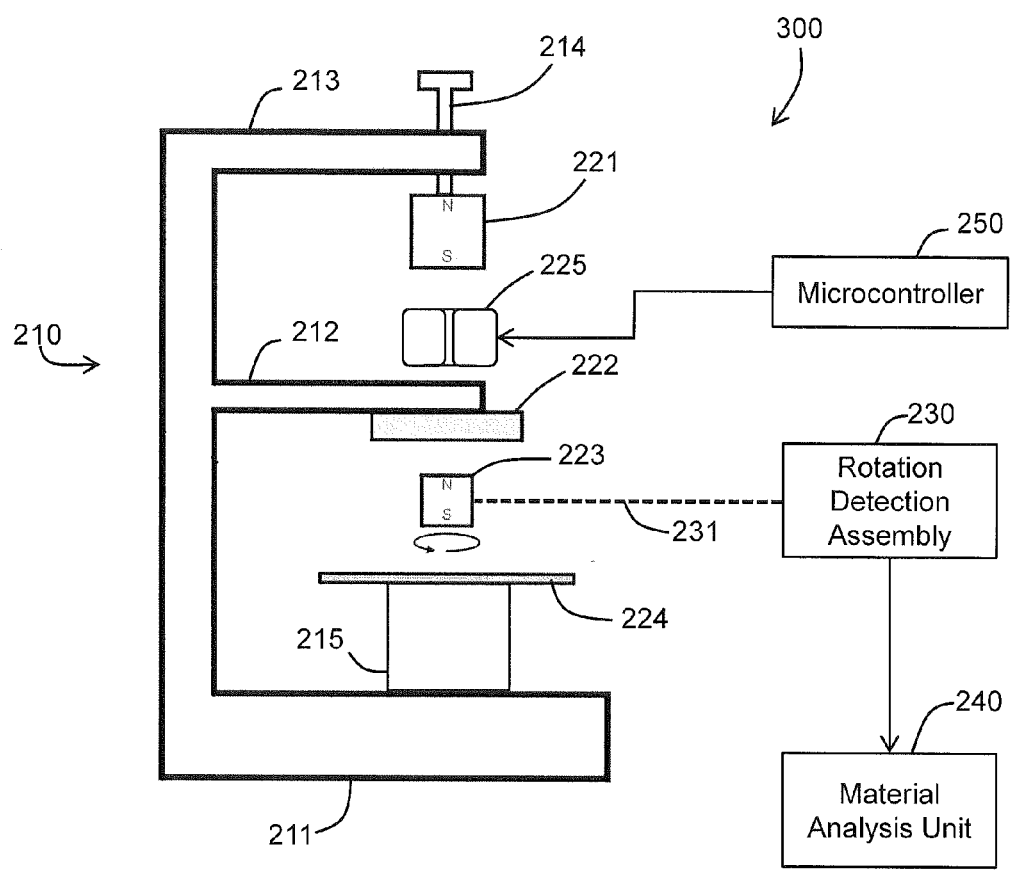
FIG. 3 illustrates a system for analyzing a material-under-test according to another embodiment of the invention.

FIG. 3 illustrates a system 300 for analyzing a material according to another embodiment of the invention. The system 300 is similar to the system 200 of FIG. 2, except the system 300 includes a stator coil 225 to cause rotation of the floating magnet 223. In operation, current is provided to the stator coil 225 by the microcontroller 250, or a power supply that is part of or controlled by the microcontroller 250, to generate a magnetic field by the stator coil 225. The magnetic field 225 may be oriented to cause rotation of the floating magnet 223. As discussed above, the rotation rate of the floating magnet 223 decreases exponentially due to the drag torque of the material-under-test 224, the rotation rate of the floating magnet 223 is detected by the rotation detection assembly 230 and the conductivity or resistivity of the material-under-test 224 is calculated by the material analysis unit 240.

Figure 4:
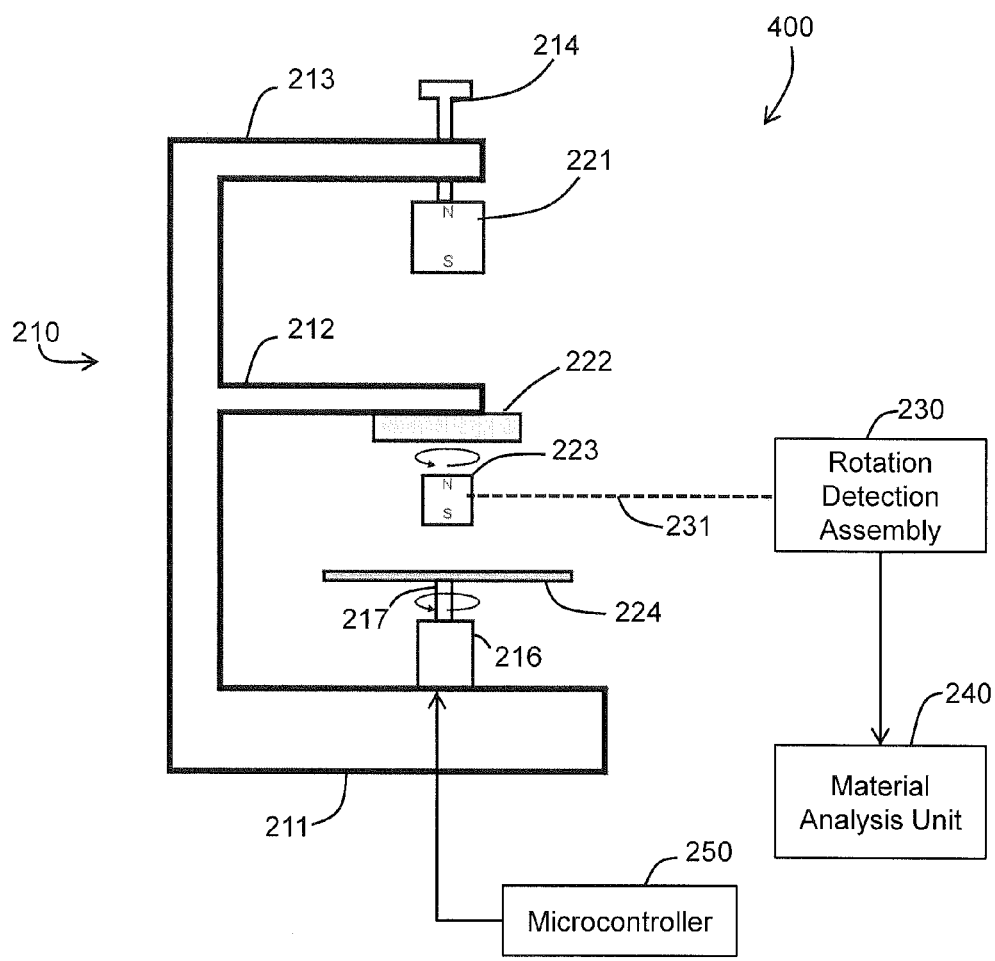
FIG. 4 illustrates a system for analyzing a material-under-test according to another embodiment of the invention.

FIG. 4 illustrates a system 400 for analyzing a material according to another embodiment of the invention. The system 400 is similar to the system 200 illustrated in FIG. 2, except that instead of maintaining the material-under-test 224 stationary, initiating rotation of the floating magnet 223 and measuring a decrease in the rotation rate of the floating magnet 223 to calculate the conductivity of the material-under-test 224, the embodiment illustrated in FIG. 4 includes rotating the material-under-test 224 and measuring a corresponding increase in the rotation rate of the floating magnet 223.

In particular, the system 400 includes a motor 216 and rotating mount 217 on which the material-under-test 224 is mounted. Floating magnet 223 is positioned above the material-under-test 224 and is maintained stationary prior to the test. Upon initiating the test, a microcontroller 250 turns on the motor 216 to rotate at a predefined rotation rate $\omega_C$. The material-under-test 224 applies drag torque to the floating magnet 223, and the floating magnet 223 begins to rotate. The rotation rate of the floating magnet 223 increases exponentially, according to the following formula:

$$\omega = \omega_C (1 - e^{-t/\tau}) \quad (3)$$

In the Equation 3, $\omega_C$ is the angular velocity of the material-under-test 224, or of the conductor on or in the material-under-test 224. The drag torque drags the floating magnet 223 to rotate faster until it reaches the terminal angular velocity of the rotating material-under-test 224. The rotation rate is measured by the rotation detection assembly 230. The sensor signals from the rotation detection assembly 230 are provided to the material analysis unit 240, which calculates the conductivity or resistivity of the material-under-test 224.

In some embodiments, the above operations are performed in a vacuum environment to eliminate additional drag on the floating magnet 223 due to ambient air. In addition, while FIGS. 2A, 2B, 3 and 4 illustrate a cubical floating magnet 223, embodiments of the invention encompass a floating magnet 223 of any shape capable of floating based on the magnetic and diamagnetic forces illustrated in FIGS. 2A, 3 and 4, and capable of providing rotation data to the rotation detection assembly 230. In one embodiment, the floating magnet 223 is a sphere having markings thereon that are detected by the rotation detection assembly 230 to detect the rotation rate of the floating magnet 223. The use of a sphere as the floating magnet 223 further reduces drag on the floating magnet 223 from ambient air.

Figure 5:
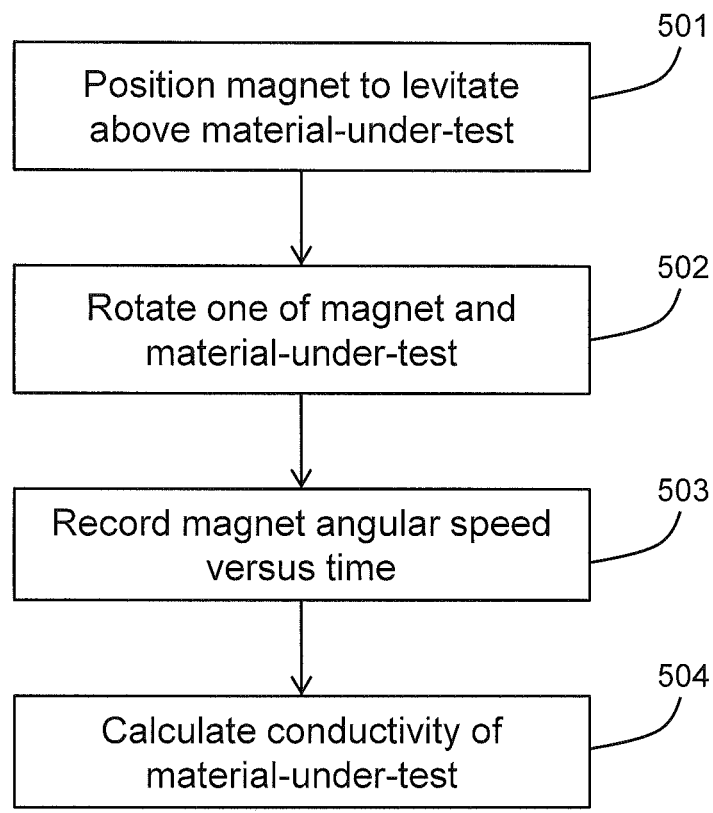
FIG. 5 illustrates a flow diagram of a method for analyzing a material according to an embodiment of the invention.

FIG. 5 is a flowchart illustrating a method according to an embodiment of the invention. In block 501, a floating magnet is positioned to levitate above a material-under-test. For example, the floating magnet may be positioned beneath a diamagnet, which is, in turn, positioned beneath a mounted magnet. The attraction of the mounted magnet may equal the repulsion of the diamagnet and gravity, causing the floating magnet to float beneath the diamagnet and above a material-under-test.

In block 502, one of the floating magnet and the material-under-test is controlled to begin rotating. For example, a force may be applied to the floating magnet while the material-under-test is maintained stationary. Alternatively, the material-under-test may be rotated while the floating magnet begins in a stationary state. In one embodiment, the floating magnet is caused to rotate by an impulse actuator, such as a solenoid, or by a stator coil. In another embodiment, the material-under-test is caused to rotate by a motor.

In block 503, the rotation rate or angular speed of the floating magnet is measured over time. For example, in an embodiment in which the material-under-test is maintained stationary, the material-under-test exerts a drag torque on the floating magnet according to the conductivity or resistivity of the material-under-test. Accordingly, the decrease in the rotation rate of the floating magnet is measured over time. Conversely, in an embodiment in which the material-under-test is rotated, the drag torque of the material-under-test causes the floating magnet to rotate, and the increase in the rotation rate of the floating magnet is measured over time.

In block 504, the conductivity or resistivity of the material-under-test is calculated based on the measured rotation rate of the floating magnet.

According to embodiments of the invention, a conductivity or resistivity of the material-under-test may be calculated without contacting the material-under-test.

As will be appreciated by one skilled in the art, aspects of the present invention may be embodied as an apparatus, system, method or computer program product. For example, the method of initiating rotation of the floating magnet or the material-under test, measuring a rotation rate and calculating the conductivity may be performed by a system controlled by a computer executing computer code that controls the system to execute the method. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention have been described with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the disclosure in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

While a preferred embodiment has been described, it will be understood that those skilled in the art, both now and in the future, may make various improvements and enhancements which fall within the scope of the claims which follow.

What is claimed is:

1. A system for analyzing a material-under-test, comprising:
    a support structure;
    a mounted magnet mounted to the support structure;
    a free-floating magnet disposed below the mounted magnet;
    a diamagnet mounted to the support structure and positioned between the mounted magnet and the free-floating magnet such that the free-floating magnet floats in the air beneath the diamagnet;
    a rotation detection assembly configured to project a laser beam to the free-floating magnet to detect a rotation rate of the free-floating magnet, the rotation rate increasing or decreasing based on a drag torque effect of a material-under-test on the free-floating magnet; and
    a conductivity calculation unit in electrical communication with the rotation detection assembly, the conductivity calculation unit configured to calculate at least one of a conductivity and a resistivity of the material-under-test based on the detected rotation rate of the free-floating magnet,
    wherein the free-floating magnet physically is not connected to the material-under-test and rotates independently with respect to the material-under-test.

2. The system of claim 1, wherein the material-under-test is stationary; and
    the conductivity calculation unit is configured to calculate at least one of the conductivity and the resistivity of the material-under-test by detecting a decrease in the rotation rate of the free-floating magnet over time.

3. The system of claim 2, further comprising:
    a solenoid disposed adjacent to the free-floating magnet, the solenoid including a coil and armature configured to apply a force to the free-floating magnet to initiate rotation of the free-floating magnet.

4. The system of claim 2, further comprising: a stator coil disposed adjacent to the free-floating magnet, the stator coil configured to generate a magnetic field to initiate rotation of the free-floating magnet.

5. The system of claim 1, wherein the material-under-test is configured to rotate, and
    the conductivity calculation unit is configured to calculate at least one of the conductivity and the resistivity of the material-under-test by detecting an increase in the rotation rate of the free-floating magnet over time.

6. The system of claim 5, further comprising a motor mounted to the support structure, the motor configured to rotate the material-under-test.

7. The system of claim 1, wherein the rotation detection assembly comprises:
    a laser emitter configured to project light onto the free-floating magnet; and
    a laser detector configured to detect light reflected from the free-floating magnet.

8. The system of claim 1, wherein the free-floating magnet is a cube.

9. The system of claim 1, wherein the free-floating magnet is a sphere, and
    the free-floating magnet includes one or more markers on a surface of the sphere that are tracked by the rotation detection assembly to detect the rotation rate of the free-floating magnet.

10. A computer program product for analyzing a material-under-test, comprising:
    a non-transitory computer readable medium having stored thereon computer code which, when executed by a processor, causes the processor to perform a method, the method comprising:
    initiating rotation of a free-floating magnet, the free-floating magnet suspended in physical non-contact between a diamagnet and a material-under-test, the diamagnet mounted to the support structure and located between the free-floating magnet and a mounted magnet to cause the free-floating magnet to float and rotate independently with respect to the material-under-test;

measuring a rotation rate of the free-floating magnet over time based on a reflection of a laser beam from the free-floating magnet, the rotation rate increasing or decreasing based on a drag torque effect of a material-under-test on the free-floating magnet; and calculating at least one of a conductivity and a resistivity of the material-under-test based on the rotation rate of the free-floating magnet.

11. The computer program product of claim 10, the method further comprising:

rotating the material-under-test; and calculating at least one of the conductivity and the resistivity of the material-under-test by measuring an increase in the rotation rate of the free-floating magnet over time.

12. The computer program product of claim 10, the method further comprising:

maintaining stationary the material-under-test;

controlling a solenoid to apply a force to the free-floating magnet to initiate rotation of the free-floating magnet; and calculating at least one of the conductivity and the resistivity of the material-under-test by measuring a decrease in the rotation rate of the free-floating magnet over time.

13. The computer program product of claim 10, the method further comprising:

maintaining stationary the material-under-test;

providing current to a stator coil to generate a magnetic field to apply a force to the free-floating magnet to initiate rotation of the free-floating magnet; and calculating at least one of the conductivity and the resistivity of the material-under-test by measuring a decrease in the rotation rate of the free-floating magnet over time.

* * * * *